(12) United States Patent
Wang et al.

(10) Patent No.: US 10,585,080 B2
(45) Date of Patent: *Mar. 10, 2020

(54) HIGH PRESSURE PROCESSING PRESSURE SENSOR

(71) Applicant: Chromatic Technologies, Inc., Colorado Springs, CO (US)

(72) Inventors: Ruizheng Wang, Colorado Springs, CO (US); Timothy J. Owen, Colorado Springs, CO (US); Lyle D. Small, Colorado Springs, CO (US)

(73) Assignee: Chromatic Technologies, Inc., Colorado Springs, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/504,696

(22) Filed: Jul. 8, 2019

(65) Prior Publication Data
US 2019/0331650 A1    Oct. 31, 2019

Related U.S. Application Data

(63) Continuation of application No. 15/712,049, filed on Sep. 21, 2017, now Pat. No. 10,345,278.

(Continued)

(51) Int. Cl.
*A23L 5/40* (2016.01)
*A23L 3/015* (2006.01)
(Continued)

(52) U.S. Cl.
CPC ............ *G01N 31/226* (2013.01); *A23L 3/015* (2013.01); *A23L 5/40* (2016.08); *G01L 7/00* (2013.01);
(Continued)

(58) Field of Classification Search
None
See application file for complete search history.

(56) References Cited

U.S. PATENT DOCUMENTS

| | | | |
|---|---|---|---|
| 3,447,945 | A | 6/1969 | Shizuo et al. |
| 4,002,060 | A | 1/1977 | Ogata et al. |

(Continued)

FOREIGN PATENT DOCUMENTS

WO    2015/148619    10/2015

OTHER PUBLICATIONS

U.S. Appl. No. 15/712,049, filed Sep. 21, 2017.
(Continued)

*Primary Examiner* — Natalie Huls
*Assistant Examiner* — Jermaine L Jenkins
(74) *Attorney, Agent, or Firm* — Craig R. Miles; CR Miles P.C.

(57) ABSTRACT

A pressure sensor and its use for visually determining whether a preselected pressure threshold has been achieved, for example during high pressure processing treatment of a foodstuff. The pressure sensor includes a contained color-changing system having a dye, a developer, and a solvent; upon achievement of the preselected pressure threshold, the dye and the developer interact, resulting in a visible color change. Further, the visible color change can be retained upon a decrease in pressure and upon an increase in temperature, thereby effectively recording the achievement of the preselected pressure threshold during the high pressure processing treatment.

22 Claims, 4 Drawing Sheets

Related U.S. Application Data

(60) Provisional application No. 62/399,103, filed on Sep. 23, 2016.

(51) Int. Cl.

| | | |
|---|---|---|
| *G01L 7/00* | (2006.01) | |
| *G01L 11/02* | (2006.01) | |
| *G01N 31/22* | (2006.01) | |
| *G01L 11/00* | (2006.01) | |
| *G01J 3/02* | (2006.01) | |

(52) U.S. Cl.
CPC ............. *G01L 11/002* (2013.01); *G01L 11/02* (2013.01); *A23V 2002/00* (2013.01); *G01J 3/0291* (2013.01); *G01N 31/22* (2013.01)

(56) References Cited

U.S. PATENT DOCUMENTS

| | | | |
|---|---|---|---|
| 4,078,423 A | 3/1978 | Ogata et al. | |
| 4,720,301 A | 1/1988 | Kito et al. | |
| 4,892,677 A | 1/1990 | Preziosi et al. | |
| 5,470,750 A * | 11/1995 | Bar-Or | G01N 33/52 436/63 |
| 6,799,467 B2 | 10/2004 | Minerich et al. | |
| 7,494,537 B2 | 2/2009 | Ono et al. | |
| 7,649,469 B2 | 1/2010 | Smith et al. | |
| 8,402,832 B2 | 3/2013 | Ribi | |
| 8,640,546 B2 | 2/2014 | Trahan et al. | |
| 8,883,049 B2 | 11/2014 | Clayton et al. | |
| 9,021,884 B2 | 5/2015 | Trahan et al. | |
| 9,175,175 B2 | 11/2015 | Clayton et al. | |
| 9,604,485 B2 | 3/2017 | Greener | |
| 9,808,798 B2 * | 11/2017 | Ismagilov | B01L 3/5027 |
| 10,345,278 B2 * | 7/2019 | Wang | |
| 2003/0127416 A1 | 7/2003 | Salazar-Leal | |
| 2010/0009042 A1 | 1/2010 | Fujikawa et al. | |
| 2010/0236682 A1 | 9/2010 | Patient et al. | |
| 2010/0326198 A1 | 12/2010 | Ribi | |
| 2011/0143458 A1 * | 6/2011 | Maegawa | G01N 33/558 436/518 |
| 2012/0079980 A1 | 4/2012 | Taylor et al. | |
| 2013/0340885 A1 | 12/2013 | Clayton et al. | |
| 2014/0013864 A1 | 1/2014 | Hichenboth et al. | |
| 2014/0048010 A1 | 2/2014 | Smith et al. | |
| 2014/0216162 A1 | 8/2014 | Trahan et al. | |
| 2014/0275381 A1 | 9/2014 | Ribi | |
| 2015/0219505 A1 | 8/2015 | Parker et al. | |
| 2016/0083586 A1 | 3/2016 | Clayton et al. | |
| 2016/0130455 A1 | 5/2016 | Ono | |
| 2016/0194132 A1 | 7/2016 | Davidson et al. | |
| 2018/0120275 A1 | 5/2018 | Wang et al. | |

OTHER PUBLICATIONS

U.S. Appl. No. 62/399,103, filed Sep. 23, 2016.
PCT International Patent Application No. PCT/US17/53070; International Search Report and Written Opinion of the International Searching Authority dated Sep. 22, 2017.
MacLaren et al. Competition between dye-developer and solvent-developer interaction in a reversible thermochromic system. J. Mater. Chem., 2003,13:1701-1704.
PCT International Patent Application No. PCT/US19/50064, filed Sep. 6, 2019.
PCT International Patent Application No. PCT/US19/50064: International Search Report and Written Opinion of the International Searching Authority dated Nov. 8, 2019.
Corresponding Mexican Patent Application No. MX/a/2019/003277: First Official Action dated Nov. 5, 2019.

* cited by examiner

ATMOSPHERIC PRESSURE

HYPREBARIC PRESSURE AT SELECTED PRESSURE THRESHOLD

ATMOSPHERIC PRESSURE

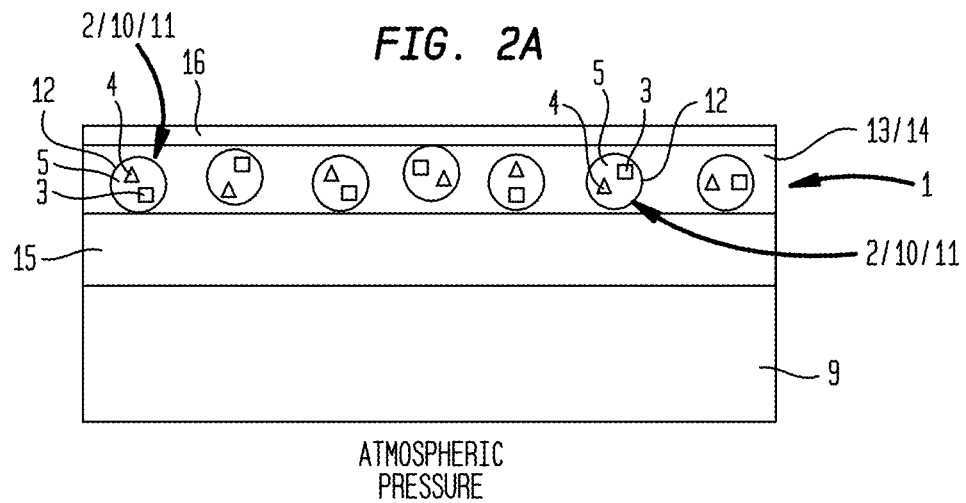
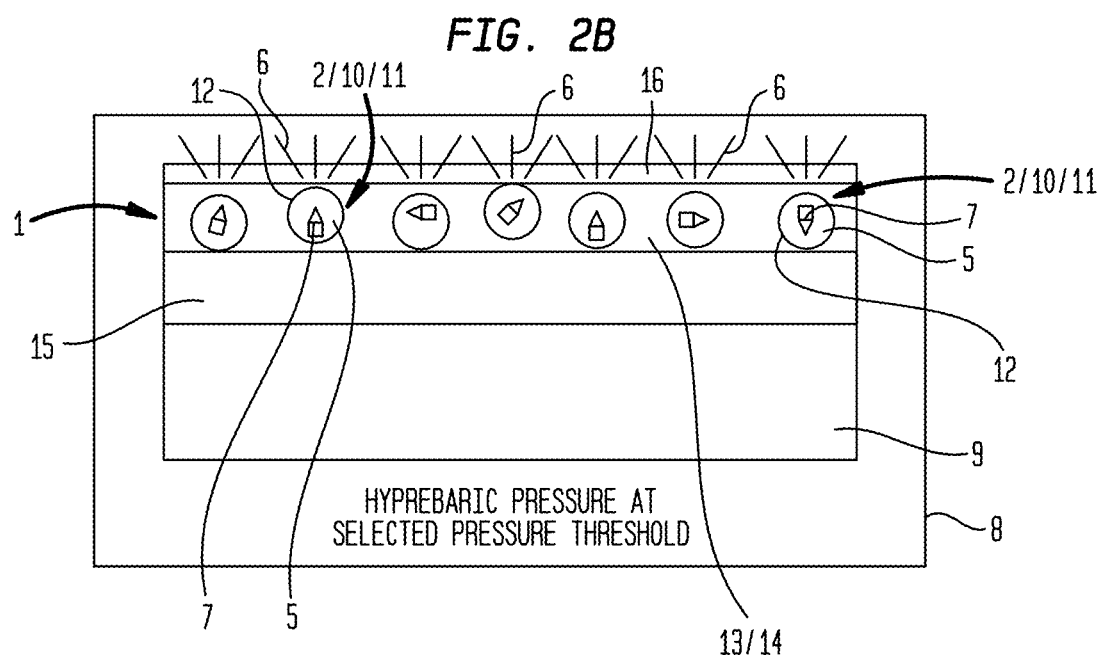
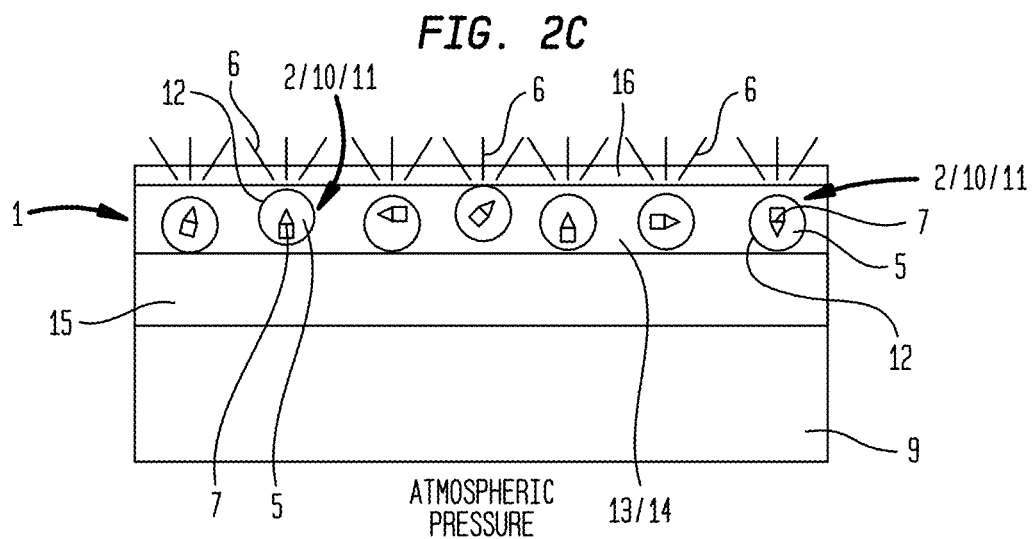

SAMPLE #1   SAMPLE #2   SAMPLE #3   SAMPLE #4   SAMPLE #5

HIGH PRESSURE PROCESSING PRESSURE SENSOR

This United States Patent Application is a continuation of U.S. patent application Ser. No. 15/712,049, filed Sep. 21, 2017, now U.S. Pat. No. 10,345,278, issued Jul. 9, 2019, which claims the benefit of U.S. Provisional Patent Application No. 62/399,103, filed Sep. 23, 2016, each hereby incorporated by reference herein.

I. SUMMARY OF THE INVENTION

A broad object of a particular embodiment of the invention can be to provide a pressure sensor including a contained color-changing system having a dye, a developer, and a solvent, whereby the developer variably interacts with the dye according to the pressure of the color-changing system. Upon achievement of a pressure threshold, the dye and the developer interact, resulting in a visible color change. Further, the visible color change can be retained upon a decrease in pressure and upon an increase in temperature, thereby effectively recording the achievement of the pressure threshold.

Another broad object of a particular embodiment of the invention can be to provide a method of using the pressure sensor (i) for visually determining whether a pressure threshold has been achieved during high pressure processing treatment of a foodstuff, or (ii) for indicating achievement of a pressure threshold during high pressure processing treatment of a foodstuff, whereby the method includes reliably associating the pressure sensor with a foodstuff. Further, the method can, but need not necessarily, include subjecting the foodstuff to high pressure processing treatment. Further, the method can, but need not necessarily, include detecting whether or not the visible color change occurred. As to particular embodiments, detecting whether or not the visible color change occurred can include visually observing the pressure sensor.

Naturally, further objects of the invention are disclosed throughout other areas of the specification, drawings, photographs, and claims.

II. A BRIEF DESCRIPTION OF THE DRAWINGS

FIG. 2A is a cross sectional view through a particular embodiment of the instant pressure sensor reliably associated with a foodstuff prior to HPP treatment and correspondingly, prior to exposure to a preselected pressure threshold, whereby the dye and the developer are not complexed and thus, the color-changing system of the pressure sensor has not undergone a visible color change.

FIG. 2B illustrates the particular embodiment of the instant pressure sensor shown in FIG. 2A upon HPP treatment and correspondingly, upon exposure to a preselected pressure threshold, whereby achievement of the preselected pressure threshold facilitates formation of a visibly colored dye-developer complex which provides a visible color change.

FIG. 2C illustrates the particular embodiment of the instant pressure sensor shown in FIG. 2B following depressurization after HPP treatment to atmospheric pressure, whereby the visibly colored dye-developer complex is stably retained and thus, continues to provide the visible color change.

III. DETAILED DESCRIPTION OF THE PREFERRED EMBODIMENTS

Figure 1A:
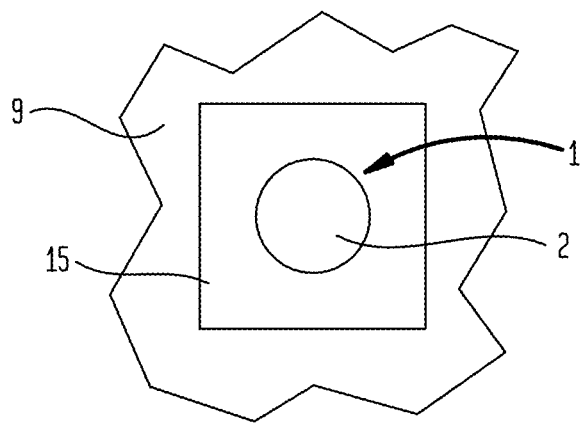
FIG. 1A is an illustration of a particular embodiment of the instant pressure sensor reliably associated with a foodstuff prior to HPP treatment and correspondingly, prior to exposure to a preselected pressure threshold, whereby the color-changing system of the pressure sensor has not undergone a visible color change.
Figure 1B:
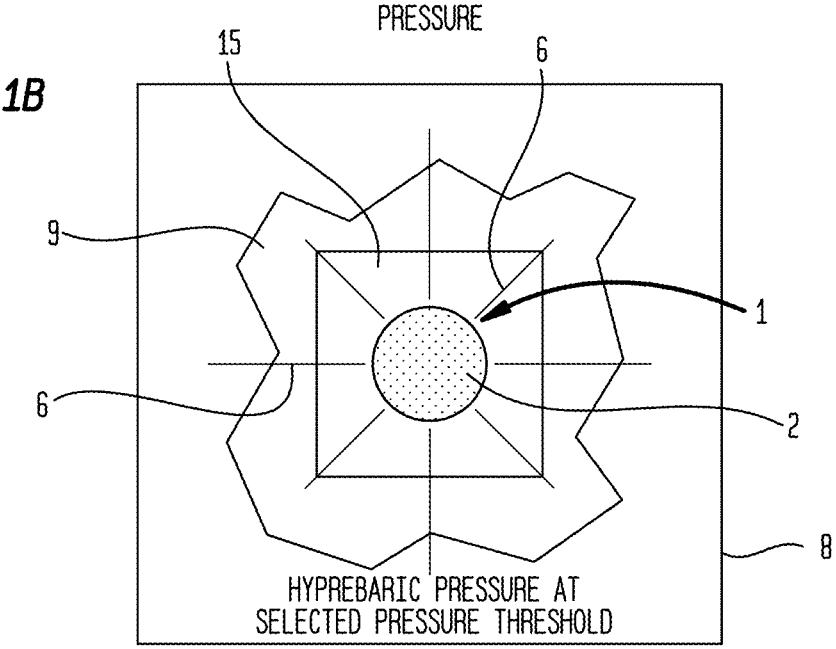
FIG. 1B is an illustration of the particular embodiment of the instant pressure sensor shown in FIG. 1A upon HPP treatment and correspondingly, upon exposure to a preselected pressure threshold, whereby the color-changing system of the pressure sensor has undergone a visible color change.
Figure 1C:
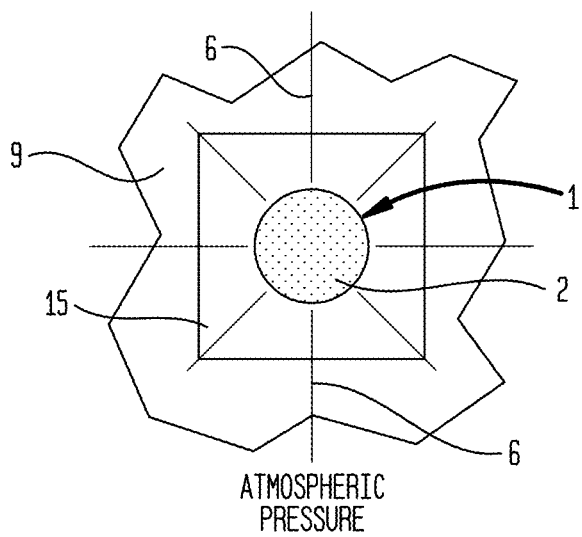
FIG. 1C is an illustration of the particular embodiment of the instant pressure sensor shown in FIG. 1B following depressurization after HPP treatment to atmospheric pressure, whereby the color-changing system of the pressure sensor retains the visible color change.

Now referring primarily to FIG. 1A through and FIG. 1C, which illustrate a method of using a particular embodiment of the inventive pressure sensor (1) for visually determining whether a preselected pressure threshold has been achieved or for indicating achievement of a preselected pressure threshold, whereby the pressure sensor (1) includes a contained color-changing system (2) comprising: a dye (3), a developer (4), and a solvent (5). The developer (4) variably interacts with the dye (3) according to the pressure of the color-changing system (2), whereby upon achievement of the preselected pressure threshold, the dye (3) and the developer (4) interact, resulting in a visible color change (6) which can be detected or visually observed.

Now referring primarily to FIG. 2A through and FIG. 2C, to elaborate on the above, interaction between the dye (3) and the developer (4) results in the formation of a visibly colored dye-developer complex (7) which can be detected or visually observed to indicate that the preselected pressure threshold has been achieved.

Accordingly, the method of use can include detecting whether or not the visible color change occurred, for example by visually observing the pressure sensor (1), whereby visual detection of the visible color change (6) resulting from the formation of the visibly colored dye-developer complex (7) indicates that the preselected pressure threshold has been achieved. Conversely, visual detection of the absence of the visible color change (6), meaning no visible color change occurred, indicates that the preselected pressure threshold has not been achieved.

High Pressure Processing

The instant pressure sensor (1) may be particularly useful for detecting and signaling that a desired pressure, referred to as the preselected pressure threshold, has been achieved within a vessel (8) such as a food-processing vessel (8). In a particularly desirable application, the vessel (8) is a pressurization vessel (8) used in high pressure processing (HPP) methods for reducing the threat posed by microbial contamination of foodstuff (9).

HPP food-processing methods are well known and described by others. Although HPP methods are known to be effective for enhancing the microbial safety of treated foodstuff (9), they have the significant drawback that HPP-treated foodstuff (9) and its associated packaging often have the same appearance before and after HPP treatment. Failure or improper operation of HPP equipment can yield foodstuff (9) which may be unsafe for consumption but has the appearance of HPP-treated foodstuff (9), even though it has not been so treated. Thus, one storing or using untreated foodstuff (9) may fail to appreciate the microbial risk present in the foodstuff (9), potentially resulting in serious illness, injury, or death. For this reason, stringent attention is often paid to product traffic control in HPP methods, to ensure that the HPP-treatment status of foodstuff (9) is accurately monitored. Such traffic control methods impose significant effort and expense, and may nevertheless fail to ensure that appropriate contamination-reduction methods have been employed. What is needed is an indicator that (i) can accompany foodstuff (9) throughout an HPP treatment regimen (i.e., such that the indicator undergoes the same treatment as the foodstuff (9)), and (ii) indicate whether the preselected pressure threshold has been achieved in the vessel (8) containing the foodstuff (9) and the indicator. The instant disclosure provides such an indicator configured as a pressure sensor (1) and methods of using the pressure sensor (1), whereby the pressure sensor (1) can be reliably associated with the foodstuff (9) undergoing HPP treatment.

Numerous methods of reliably associating an indicating device with foodstuff (9) undergoing processing are known (e.g., devices and mechanisms for adhering, tying, bundling, hanging, wrapping, stuffing, mixing, interleaving, or co-packaging devices and foodstuff (9) on, to, from, or with one another or on, to, from, or with common racks, packages, pallets, and the like) and can be used to reliably associate the pressure sensor (1) described herein with one or more foodstuffs (9) for co-processing via HPP treatment.

Advantageously, the pressure sensor (1) and methods described herein provide a convenient, preferably direct visual, indication or confirmation that a foodstuff (9) subjected to HPP treatment has been subjected to the preselected pressure threshold. This relatively simple means of confirmation reduces the need for cumbersome and expensive methods of providing traffic control for HPP-treated foodstuff (9), and can prevent unintentional bypass of HPP treatment.

Definitions

As used herein, the term "sensor" means a composition or an apparatus which detects or measures a stimulus and reacts to it in a particular way.

As used herein, the term "contained" indicates that the dye (3), the developer (4), and the solvent (5) are continuously kept within a physical proximity which allows interaction between the compounds. Additionally, by being contained, the color-changing system (2) is separated from the external environment, which may damage or destroy the color-changing system (2).

As used herein, the term "preselected" means predetermined or decided in advance.

As used herein, the term "threshold" means the point which must be obtained or exceeded for a certain phenomenon to occur or be manifested.

As used herein, the term "dye" means a chemical compound which can change color, such as a color former which is capable of reacting with the instant developer (4) to form a dye-developer complex (7) which exhibits optical properties that can be discerned by the human eye.

As used herein, the term "developer" means a chemical compound which is capable of reacting with the instant dye (3) to form a dye-developer complex (7) which exhibits optical properties that can be discerned by the human eye. The term "developer" can be synonymous with "color developer", both meaning a chemical compound which facilitates a change in color of the dye (3).

As used herein, the term "solvent" can, but need not necessarily, be synonymous with phase-change material, whereby phase-change material is herein defined simply as a material which changes from one phase to another.

As used herein, the term "foodstuff" means a good, item, or article that is consumable (including edible or drinkable) or is useful as an ingredient for making a consumable item or article. Non-limiting examples of foodstuffs (9) include fruits, juices, vegetables, grains, flours, milks, yogurts, sweetened beverages, meats, processed foods, medicaments, and the like.

As used herein, the term "detect" and forms thereof means to discover or ascertain the presence of.

Two objects, such as a foodstuff (9) and the instant pressure sensor (1), subjected to HPP treatment are "reliably associated" if the association between the two objects can be expected not to be disrupted by subjecting the reliably associated objects to the HPP treatment. Non-limiting examples of such reliable associations include adhering one object to another, tying the two objects together, containing both objects in a container, printing one object (for example the pressure sensor (1) configured as a printing ink) on packaging material or a container used to contain the other object (for example the foodstuff (9)), affixing one object (for example the pressure sensor (1)) to packaging material or a container used to contain the other object (for example the foodstuff (9)), and laminating one object (for example the pressure sensor (1)) in a portion of a packaging material used to enclose the other object (for example the foodstuff (9)).

Pressure Sensor-Foodstuff Assembly

As stated above, the instant disclosure provides a pressure sensor (1) for use together with one or more foodstuffs (9) in an HPP method.

In an important embodiment, the instant disclosure relates to an assembly for indicating achievement of the preselected pressure threshold in an HPP method for treating a foodstuff (9), whereby the assembly includes the foodstuff (9) reliably associated with the pressure sensor (1) described herein, as shown in FIG. 1A through FIG. 2C.

HPP equipment typically uses a working fluid, most commonly water. Such equipment generally includes a pressure chamber such as a vessel (8) into which a foodstuff (9) or the instant assembly can be placed. After loading (i.e., placement of the foodstuff (9) or the instant assembly within the vessel (8)), the vessel (8) is filled with the working fluid, and the vessel (8) is pressurized by application of a high hydrostatic pressure (e.g., about 29,000 psi to about 145,000 psi, more typically about 29,000 psi to about 87,000 psi) to the working fluid.

Because pressure within the working fluid in the vessel (8) is uniform throughout the working fluid, and because the working fluid in an operating HPP apparatus completely surrounds the foodstuff (9) or the instant assembly, the hydrostatic pressure within the vessel (8) is applied isotropically (i.e., not in any particular direction more than another) to the foodstuff (9) or the instant assembly. So long as the foodstuff (9) or the instant assembly does not contain compressible materials (e.g., gases such as air bubbles, as water and other fluids tend to be substantially incompressible at HPP pressures), the shape of the foodstuff (9) or the instant assembly tends not to be altered significantly (even though some microscopic changes may occur, such as denaturation of proteins within the foodstuff (9)). Furthermore, foodstuff (9) that does not include portions capable of withstanding deformation at the preselected pressure threshold will also transmit the pressure within the foodstuff (9), the result being that the hydrostatic pressure applied to the vessel (8) occurs throughout the treated foodstuff (9) or the instant assembly.

Maintenance of the foodstuff (9) at the preselected pressure threshold results in damage to microorganisms (e.g., bacteria, mold, yeast, parasites, or the like) that may be present on or within the foodstuff (9). Regardless of the precise nature of the damage, microorganisms subjected to HPP treatment appear to replicate and metabolize at substantially lower rates than non-HPP-treated microorganisms. This effect is the primary basis for the desirability of HPP treatment of foodstuff (9).

Pressure Sensor

Simply summarized again, and as shown in FIG. 1A through FIG. 2C, the pressure sensor (1), which may take the form of a composition or an apparatus, includes a contained color-changing system (2) comprising a dye (3), a developer (4), and a solvent (5). The developer (4) variably interacts with the dye (3) according to the pressure of the color-changing system (2), whereby upon achievement of the preselected pressure threshold, the dye (3) and the developer (4) interact, resulting in a visible color change (6) which can be detected or visually observed.

Dye and Developer

The instant color-changing system (2) can be a reversible color-changing system, meaning that the visible color change can be reversible, as opposed to an irreversible color change or a permanent color change.

Following, as to particular embodiments, the dye (3) of the instant color-changing system (2) can comprise a leuco dye (3) which can reversibly change between two forms, one of which is typically colorless or substantially colorless.

As but only a few non-limiting examples for the purpose of illustration, the leuco dye (3) can be: crystal violet lactone (CAS No.: 1552-42-7); Pigment Blue 63 (CAS No.: 16521-38-3); 2'-(dibenzylamino)-6'-(diethylamino)fluoran (CAS No.: 34372-72-0); or the like.

As to particular embodiments, the leuco dye (3) can be an electron-donating compound (or proton-accepting compound). Further, the developer (4) can comprise an electron-accepting compound (or proton-donating compound), such as an acid and particularly, a weak acid. Upon interaction (specifically, an electron transfer reaction) between the electron-donating leuco dye (3) and the electron-accepting developer (4), the leuco dye (3) reversibly changes color, for example from a colorless or substantially colorless state to a visibly colored state.

As but only a few non-limiting examples for the purpose of illustration, the developer (4) can be: 3,5-di-tert-butyl-catechol (CAS No.: 1020-31-1); 4,4'-(1,3-dimethylbutyl-idene)diphenol (CAS No.: 1020-31-1); 2,2'-biphenol (CAS No.: 1806-29-7); or the like.

Without being bound by any particular theory of operation, it is believed that within the instant color-changing system (2), upon achievement of the preselected pressure threshold, the developer (4) reversibly interacts with the leuco dye (3) via an electron transfer reaction to open up the lactone ring of the leuco dye (3) and stabilize the opened structure, forming a supramolecular visibly colored dye-developer complex (7), to which the visible color change (6) is attributable. When open, the lactone ring is cationic in nature, thereby extending conjugation of its π electrons and allowing absorption in the visible spectrum to provide the visibly colored dye-developer complex (7), whereby the stability of the visibly colored dye-developer complex (7) is determined, at least in part, by the affinity of the developer (4) for the leuco dye (3).

Solvent

The instant color-changing system (2) further includes a solvent (5) which effects or controls the reversible interaction between the leuco dye (3) and the developer (4).

As to particular embodiments, a solvent (5) which may be useful for the instant color-changing system (2) can be (i) a solvent (5) in which both the dye (3) and the developer (4) are soluble, and (ii) a solvent (5) which is capable of being contained along with the dye (3) and the developer (4), for example within a capsule or microcapsule (10) to provide a corresponding encapsulated or microencapsulated color-changing system (11). When contained within the capsule or microcapsule (10), the solvent (5) can facilitate the interaction between the leuco dye (3) and the developer (4).

As to particular embodiments, the solvent (5) can be a hydrocarbon.

As to particular embodiments, the solvent (5) can be a ketone.

As to particular embodiments, the ketone can have formula I as follows:

As to particular embodiments, the ketone can have formula I, whereby R' and R" can be either the same or different, and R' and R" can be (i) a straight-chain, branched, or cyclic alkyl group, (ii) a straight-chain, branched, or cyclic alkenyl group, (iii) a straight-chain, branched, or cyclic alkynyl group, (iv) an aryl group, or (v) a heteroaryl group, whereby any of the groups can be unsubstituted or substituted.

As to particular embodiments, the solvent (5) can be an ester.

As to particular embodiments, the ester can have formula II as follows:

As to particular embodiments, the ester can have formula II, whereby R' and R" can be either the same or different, and R' and R" can be (i) a straight-chain, branched, or cyclic alkyl group, (ii) a straight-chain, branched, or cyclic alkenyl group, (iii) a straight-chain, branched, or cyclic alkynyl group, (iv) an aryl group, or (v) a heteroaryl group, whereby any of the groups can be unsubstituted or substituted.

As to particular embodiments, the solvent (5) can be an alcohol.

As to particular embodiments, the alcohol can be an aliphatic alcohol, an aromatic alcohol, or combinations thereof.

As to particular embodiments, the solvent (5) can be a single compound.

As to other particular embodiments, the solvent (5) can be a mixture of two or more compounds. As to particular embodiments, the solvent (5) can be a mixture of two or more of the illustrative solvents (5) described above.

Without being bound by any particular theory of operation, it is believed that within the instant color-changing system (2), the developer (4) can also interact with the solvent (5) to form a solvent-developer complex, whereby this interaction is determined, at least in part, by the affinity of the developer (4) for the solvent (5).

Following, it may be hypothesized that the visible color change (6) can be linked to a competition between the leuco dye (3) and the solvent (5) for complexing with the developer (4), whereby the developer (4) forms a complex with the molecule(s) which it has a greater affinity for.

It should be understood that once a complex forms, the complex is stable until an amount of energy which is sufficient to destabilize the complex is input into the system, thereby dissociating the components of the complex.

Relating to the instant pressure sensor (1), at pressures lesser than or below the preselected pressure threshold, such as at atmospheric pressure, the developer (4) can have a greater affinity for the solvent (5) than for the leuco dye (3) and accordingly, the solvent-developer complex can be favored over the visibly colored dye-developer complex (7). Thus, the developer (4) is precluded from interacting with the leuco dye (3) to produce the visible color change and correspondingly, the lactone ring is closed and the leuco dye (3) is colorless or substantially colorless at pressures lesser than or below the preselected pressure threshold.

Conversely, upon achievement of the preselected pressure threshold, the developer (4) has a greater affinity for the leuco dye (3) than for the solvent (5); hence, the visibly colored dye-developer complex (7) is formed and stabilized, producing the visible color change (6).

Color Memory

As described above, the instant color-changing system (2) can be susceptible to a pressure-modulated color change. Furthermore, the instant color-changing system (2) can have a color-memory property whereby after the visibly colored dye-developer complex (7) is formed upon achievement of the preselected pressure threshold, the visibly colored dye-developer complex (7) remains stable upon a decrease in pressure from the preselected pressure threshold, for example to a pressure lesser than or below the preselected pressure threshold, including at atmospheric pressure; hence, the visible color change (6) can be retained at pressures lesser than or below the preselected pressure threshold. Correspondingly, the pressure sensor (1) can effectively record the achievement of the preselected pressure threshold, which is in contrast to conventional pressure indicators, which may only indicate the current pressure and may not indicate pressures which the pressure indicator was exposed to prior to exposure to the current pressure.

In addition to being susceptible to a pressure-modulated color change, the instant color-changing system (2) can be a thermochromic color-changing system (2) which can be susceptible to a temperature-modulated color change.

As to particular embodiments, the instant thermochromic color-changing system (2) can be a reversible thermochromic color-changing system (2), whereby the temperature-modulated color change can be reversible, as opposed to an irreversible color change or a permanent color change.

The instant reversible thermochromic color-changing system (2) can have a color-memory property whereby after the visibly colored dye-developer complex (7) is formed upon achievement of the preselected pressure threshold, the visibly colored dye-developer complex (7) remains stable (i) upon a decrease in pressure from the preselected pressure threshold and (ii) upon an increase in temperature; hence, the visible color change (6) can be retained. Correspondingly, the pressure sensor (1) can effectively record the achievement of the preselected pressure threshold even upon an increase in temperature.

The color-memory property of the instant reversible thermochromic color-changing system (2) can be imparted, at least in part, by a solvent (5) which is pressure-sensitive and condenses in volume upon an increase in pressure. Without being bound by any particular theory of operation, it is believed that an increase in pressure alters the coloration temperature of the reversible thermochromic color-changing system (2). For example, upon an increase in pressure, the coloration temperature of the reversible thermochromic color-changing system (2) correspondingly increases.

Thus, the instant reversible thermochromic color-changing system (2) can include a coloration temperature at which the reversible thermochromic color-changing system (2) changes from a substantially colorless state to a visibly colored state. Also, the instant reversible thermochromic color-changing system (2) can include a decoloration temperature at which the reversible thermochromic color-changing system (2) changes from the visibly colored state to the substantially colorless state.

Significantly, the coloration and decoloration temperatures of the instant reversible thermochromic color-changing system (2) can be different, meaning that the coloration temperature can be discrete from the decoloration temperature. For example, the coloration temperature can be less than the decoloration temperature.

Consequently, the color-memory property of the instant reversible thermochromic color-changing system (2) can facilitate retention of the visible color change upon an increase in temperature from the coloration temperature to a temperature greater than or above the coloration temperature. Additionally, the color-memory property of the instant reversible thermochromic color-changing system (2) can facilitate retention of the visibly colored state upon an increase in temperature from the coloration temperature to a temperature greater than or above the coloration temperature.

As to particular embodiments, the coloration temperature can differ from the decoloration temperature by at least about 10 Celsius degrees, meaning that the decoloration temperature can be at least about 10 Celsius degrees greater than the coloration temperature.

As to particular embodiments, the coloration temperature can differ from the decoloration temperature by at least one selected from the group including or consisting of: at least about 5 Celsius degrees, at least about 10 Celsius degrees, at least about 15 Celsius degrees, at least about 20 Celsius degrees, at least about 25 Celsius degrees, at least about 30 Celsius degrees, at least about 35 Celsius degrees, at least about 40 Celsius degrees, at least about 45 Celsius degrees, at least about 50 Celsius degrees, at least about 55 Celsius degrees, at least about 60 Celsius degrees, at least about 65 Celsius degrees, at least about 70 Celsius degrees, at least about 75 Celsius degrees, at least about 80 Celsius degrees, at least about 85 Celsius degrees, at least about 90 Celsius degrees, at least about 95 Celsius degrees, at least about 100 Celsius degrees, and greater than about 100 Celsius degrees.

As to particular embodiments, the coloration temperature can be associated with the freezing point of the reversible thermochromic color-changing system (2). Accordingly, the instant reversible thermochromic color-changing system (2)

can include (i) a freezing point at which the reversible thermochromic color-changing system (2) changes from a substantially colorless state to a visibly colored state. Moreover, the instant reversible thermochromic color-changing system (2) can include a melting point at which the reversible thermochromic color-changing system (2) changes from the visibly colored state to the substantially colorless state.

Significantly, the freezing and melting points of the instant reversible thermochromic color-changing system (2) can be different, meaning that the freezing point can be discrete from the melting point. For example, the freezing point can be less than the melting point.

Consequently, the color-memory property of the instant reversible thermochromic color-changing system (2) can facilitate retention of the visible color change upon an increase in temperature from the freezing point to a temperature greater than or above the freezing point. Additionally, the color-memory property of the instant reversible thermochromic color-changing system (2) can facilitate retention of the visibly colored state upon an increase in temperature from the freezing point to a temperature greater than or above the freezing point.

As to particular embodiments, the freezing point can differ from the melting point by at least about 10 Celsius degrees, meaning that the melting point can be at least about 10 Celsius degrees greater than the freezing point.

As to particular embodiments, the freezing point can differ from the melting point by at least one selected from the group including or consisting of: at least about 5 Celsius degrees, at least about 10 Celsius degrees, at least about 15 Celsius degrees, at least about 20 Celsius degrees, at least about 25 Celsius degrees, at least about 30 Celsius degrees, at least about 35 Celsius degrees, at least about 40 Celsius degrees, at least about 45 Celsius degrees, at least about 50 Celsius degrees, at least about 55 Celsius degrees, at least about 60 Celsius degrees, at least about 65 Celsius degrees, at least about 70 Celsius degrees, at least about 75 Celsius degrees, at least about 80 Celsius degrees, at least about 85 Celsius degrees, at least about 90 Celsius degrees, at least about 95 Celsius degrees, at least about 100 Celsius degrees, and greater than about 100 Celsius degrees.

Figure 3:
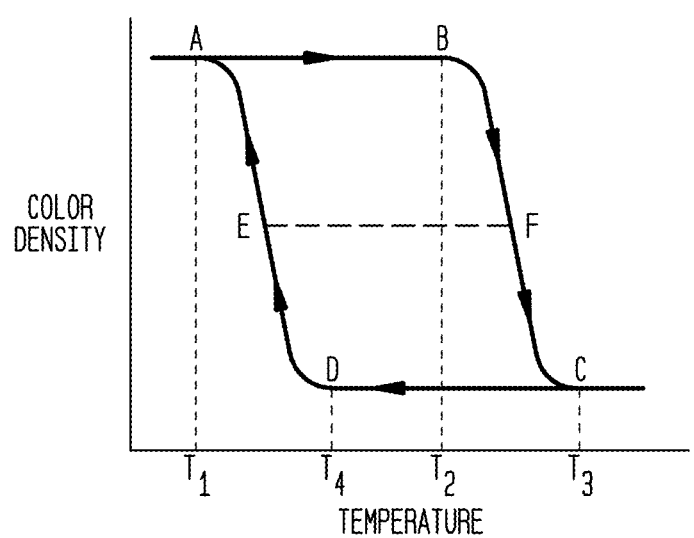
FIG. 3 is an illustration of hysteresis characteristics of a particular embodiment of the instant thermochromic color-changing system which has a color-memory property.

Now referring primarily to FIG. 3, hysteresis characteristics of a particular embodiment of the instant reversible thermochromic color-changing system (2) having the color-memory property can be described by illustrating the dependence of color density on temperature whereby as stated above, it is herein instantly recognized that the coloration temperature of the reversible thermochromic color-changing system (2) can be altered by pressure and in particular, the coloration temperature increases upon an increase in pressure.

Again referring primarily to FIG. 3, the y axis shows the color density and the x axis shows the temperature. The color density of the reversible thermochromic color-changing system (2) changes with temperature along the curve in the direction shown by the arrow marks. Point A indicates the color density at the maximum temperature $T_1$ for achieving the completely colored state (whereby $T_1$ is the complete coloration temperature). Point B indicates the color density at the maximum temperature $T_2$ for retention of the completely colored state (whereby $T_2$ is the decoloration initiation temperature). Point C indicates the color density at the minimum temperature $T_3$ for achieving a completely decolored or colorless state (whereby $T_3$ is the complete decoloration temperature). Point D indicates the color density at the minimum temperature $T_4$ for retention of the completely decolored or colorless state (whereby $T_4$ is the coloration initiation temperature).

Again referring primarily to FIG. 3, while both the completely colored state and the completely decolored or colorless state can exist between $T_2$ and $T_4$, the state retained is dependent upon the state previously achieved. For example, if the completely colored state was previously achieved upon exposure to $T_1$, the completely colored state will be retained until exposure to a temperature equal to or greater than $T_2$. Alternatively, if the completely decolored or colorless state was previously achieved upon exposure to $T_3$, the completely decolored or colorless state will be retained until exposure to a temperature equal to or lesser than $T_4$.

As to particular embodiments, the colored state or the decolored or colorless state can be retained upon exposure to temperatures between about 5 Celsius degrees to about 100 Celsius degrees from the temperature at which the colored state or the decolored or colorless state was achieved. Said another way, the length of segment EF shown in FIG. 3, which represents the temperature range width indicating the degree of hysteresis or hysteresis range or hysteresis window ΔH, can be in a range of between about 5 Celsius degrees to about 100 Celsius degrees.

As but one illustrative example relating to HPP, upon achievement of the preselected pressure threshold, the thermochromic color-changing system (2) can undergo a visible color change (6) and be completely colored at $T_1$. Following, the completely colored state can be retained upon a decrease in pressure, for example upon a decrease in pressure to atmospheric pressure. Further, the completely colored state can be retained upon heating, as the visibly colored dye-developer complex (7) remains stable until temperature $T_2$ is reached.

As to particular embodiments, $T_1$ may, but need not necessarily, be a temperature lesser than about 20° Celsius. For example, $T_1$ may, but need not necessarily, be a temperature between about −30° Celsius to about 20° Celsius.

As to particular embodiments, $T_2$ may, but need not necessarily, be a temperature greater than about 30° Celsius. For example, $T_2$ may, but need not necessarily, be a temperature between about 30° Celsius to about 90° Celsius.

Phase Change Material

As to particular embodiments, the solvent (5) can be a phase change material which changes between a liquid phase (or a substantially liquid phase) and a solid phase (or a substantially solid phase) according to the pressure of the color-changing system (2).

As to particular embodiments, the solvent (5) can change from a liquid phase to a solid phase upon achievement of the preselected pressure threshold.

As to particular embodiments, the solid phase of the solvent (5) can facilitate or enable the interaction between the leuco dye (3) and the developer (4), whereby the visibly colored dye-developer complex (7) can be a crystalized structure having an extended conjugation of its π electrons. Thus, upon achievement of the preselected pressure threshold, the visibly colored dye-developer complex (7) is formed, resulting in the visible color change (6) which can be detected or visually observed.

In contrast, the liquid phase of the solvent (5), which can exist at pressures lesser than or below the preselected pressure threshold, can preclude the interaction between the leuco dye (3) and the developer (4), rendering the leuco dye (3) colorless or substantially colorless.

Of note, because of the color-memory property of the color-changing system (2), after achievement of the preselected pressure threshold, the visibly colored dye-developer complex (7) can remain stable even when the solvent (5) is in the liquid phase (for example, upon a decrease in pressure) until temperature $T_2$ is reached, as only a temperature equal to or above temperature $T_2$ inputs an amount of energy into the system which is sufficient to destabilize the visibly colored dye-developer complex (7).

Microcapsules

As stated above, the instant color-changing system (2) is contained, meaning that the dye (3), the developer (4), and the solvent (5) are continuously kept within a physical proximity which allows interaction between the compounds. Additionally, by being contained, the color-changing system (2) is separated from the external environment, which may damage or destroy the color-changing system (2).

Now referring primarily to FIG. 2A through FIG. 2C, as to particular embodiments, the color-changing system (2) can be encapsulated within a capsule or microcapsule (10) to provide a corresponding encapsulated or microencapsulated color-changing system (11), whereby the capsule or microcapsule (10) can have a diameter in a range of between about 300 nanometers to about 100 microns, depending upon the embodiment.

The capsule or microcapsule wall (12) which forms the capsule or microcapsule (10) around the color-changing system (2) can be formed from any of a numerous and wide variety of polymers, such as melamine formaldehyde resin (CAS No.: 9003-08-01); polyurethane resin (CAS No.: 9009-54-5); acrylic resin, or the like.

Of note, the capsule or microcapsule wall (12) need not rupture or burst for the visible color change (6) to occur, which is in stark contrast to conventional pressure-indicating systems which require that their capsule or microcapsule wall (12) rupture or burst for a visible color change (6) to occur. For example, a conventional pressure-indicating system may include a color former and a color developer, at least one of which is encapsulated to separate it from the other, thereby precluding the color former and the color developer from interacting. Following, the capsule or microcapsule wall (12) must rupture or burst to permit the color former and the color developer to be within a physical proximity which allows interaction between the compounds, resulting in a visible color change (6). For example, upon rupturing or bursting of the capsules or microcapsules, the color former is released therefrom, contacts and reacts with the color developer, and forms a colored product which can be visually detected.

Said another way due to significance, it is not required or necessary for the capsule or microcapsule wall (12) which contains the instant color-changing system (2) to rupture or burst for the visibly colored dye-developer complex (7) to form and correspondingly, for the visible color change (6) to occur.

As to particular embodiments, it can be required that the capsule or microcapsule wall (12) does not rupture or burst for the visible color change (6) to occur. In other words, the visible color change (6) can only occur if the capsule or microcapsule wall (12) remains intact, thereby functioning to contain the color-changing system (2).

Notably, because the capsule or microcapsule wall (12) which contains the instant color-changing system (2) need not rupture for the visibly colored dye-developer complex (7) to form, the visible color change (6) occurs whether the pressure applied to the encapsulated or microencapsulated color-changing system (11) is isotropic or anisotropic. This is another significant difference between the instant pressure sensor (1) and conventional pressure indicators which typically change color only upon the application of anisotropic pressure.

The properties of the capsule or microcapsule wall (12), such as its composition, rigidity, flexibility, wall thickness, size (corresponding to the diameter of the capsule or microcapsule), etc., can be chosen to result in an encapsulated or microencapsulated color-changing system (11) which visibly changes color at the preselected pressure threshold, which can be chosen according to the particular circumstances, including the particular foodstuff being treated by HPP.

Coating

As to particular embodiments of the pressure sensor (1), the encapsulated or microencapsulated color-changing system (11) can be incorporated into a coating (13). As but one illustrative example, the encapsulated or microencapsulated color-changing system (11) can be incorporated into an ink (14).

As to particular embodiments, the ink (14) can be selected from the group including or consisting of: flexographic inks, gravure inks, offset inks, and screen inks. The ink (14) can be water-based, solvent-based, UV-curable, wet, dry, or combinations thereof, depending upon the application.

As but only a few non-limiting examples for the purpose of illustration, the ink (14) can comprise: an acrylic solution; an acrylic emulsion; a sulfonated polyester; or the like.

As to particular embodiments, the ink (14) can be specifically formulated for application to a substrate (15) via printing, such as printing onto a substrate (15) configured as packaging material designed for HPP.

Substrate

As to particular embodiments of the pressure sensor (1), the encapsulated or microencapsulated color-changing system (11) can be coupled to a substrate (15), which can be formed from any of a numerous and wide variety of materials.

Importantly, the substrate (15) can, but need not necessarily, be flexible, meaning capable of being bent relatively easily, for example manually or by hand. This is in contrast to a rigid material, which is not able to be bent easily or which is not able to be bent without breaking. Of course, as to particular embodiments, the substrate (15) can be rigid without departing from the scope and spirit of the invention.

Additionally, as to particular embodiments, the pressure sensor (1) can, but need not necessarily, further include a cover (16) which covers the encapsulated or microencapsulated color-changing system (11) coupled to the substrate (15), thus disposing the encapsulated or microencapsulated color-changing systems (11) between the substrate (15) and the cover (16).

The cover (16) may be used for aesthetic reasons or for safety reasons, for example when it is desirable to prevent contact between elements of the pressure sensor (1) and the foodstuff (9), either directly or through common contact with the working fluid of the HPP method. In some instances, it may be desirable to prevent contact between the encapsulated or microencapsulated color-changing system (11) or the pressure sensor (1) and the working fluid by containing the pressure sensor (1) within a material that is substantially impermeable to the working fluid, such as a waterproof or water-resistant material.

The precise shapes and conformations of the substrate (15) and the cover (16) are not critical. However, some embodiments lend themselves to easier manufacture and assembly. For example, in one embodiment, the substrate (15) and the cover (16) have the form of a sheet (i.e., the substrate (15) and the cover (16) are configured as two sheets opposed adjacent one another). The substrate (15) and the cover (16) can have approximately the same thickness or different thicknesses, such as each being a plastic film having a thickness of about 2 to 50 mils.

The materials from which each of the substrate (15) and the cover (16) are made is substantially immaterial, other than that substrate (15) should be sufficient to support the encapsulated or microencapsulated color-changing system (11) and the cover (16) should be sufficient to cover the encapsulated or microencapsulated color-changing system (11). By way of example, each of the substrate (15) and the cover (16) can be a polyester film having a thickness of about 2 to 10 mils. Preferably, at least one of the substrate (15) and the cover (16) is transparent.

At least one of the substrate (15) and the cover (16) can have a viewing portion adapted to permit detection of the visible color change (6) associated with formation of the visibly colored dye-developer complex (7), for example by visual observation of the pressure sensor (1) (i.e., not requiring disassembly of the pressure sensor (1)). Alternatively, the pressure sensor (1) can be disassembled to determine whether the visibly colored dye-developer complex (7) formed. As to particular embodiments, at least one of the substrate (15) and the cover (16) is sufficiently transparent or translucent that the visible color change (6) associated with formation of the visibly colored dye-developer complex (7) can be detected by direct visual observation of the viewing portion.

As to particular embodiments, one or both of the substrate (15) and cover (16) can act as a packaging material or package, or a component thereof, for containing a foodstuff (9). The substrate (15), the cover (16), or both can be an integral part of the packaging material (i.e., unitary with the packaging material such that removal of the substrate (15) or the cover (16) would compromise the integrity of the packaging material and its function of separating its interior from the external environment). Alternatively, the substrate (15), the cover (16), or both can be separable (e.g., tearable, detachable, or peelable) from the packaging material.

If only one of the substrate (15) and the cover (16) is a part of the packaging material, the pressure sensor (1) device can be preferably configured such that no fluid communication occurs between the encapsulated or microencapsulated color changing system (11) and the cavity of the packaging material containing the foodstuff (9) when the packaging material is intact. Such a configuration reduces the likelihood that capsules or microcapsules (10) or the components of the color-changing system (2) contained within the capsules or microcapsules (10) will contact a foodstuff (9) packed within the packaging material.

As to particular embodiments, the capsules or microcapsules (10) which contain the color-changing system (2) can be bound to the substrate (15), to the cover (16), or to both, either directly or by way of a binding agent.

Alternatively, as to other particular embodiments, the capsules or microcapsules (10) which contain the color-changing system (2) can be kept proximate to, but not necessarily bound to any surface of, the substrate (15) or the cover (16).

Range of Preselected Pressure Thresholds

The dye (3) and the developer (4) of the instant contained color-changing system (2) can interact to form the visibly colored dye-developer complex (7) and provide a visible color change (6) upon the achievement of any of a numerous and wide variety of preselected pressure thresholds, depending upon the application. For example, the preselected pressure threshold can be in a range of between at least about 10,000 psi to about 100,000 psi.

As to particular embodiments, the preselected pressure threshold can be about 10,000 psi or at least about 10,000 psi; correspondingly, the dye (3) and the developer (4) can interact to form the visibly colored dye-developer complex (7) and provide a visible color change (6) when exposed to a pressure of about 10,000 psi or at least about 10,000 psi, thereby indicating that the pressure sensor (1) and any foodstuff (9) with which it is reliably associated have been exposed to a pressure of about 10,000 psi or at least about 10,000 psi.

As to particular embodiments, the preselected pressure threshold can be about 20,000 psi or at least about 20,000 psi; correspondingly, the dye (3) and the developer (4) can interact to form the visibly colored dye-developer complex (7) and provide a visible color change (6) when exposed to a pressure of about 20,000 psi or at least about 20,000 psi, thereby indicating that the pressure sensor (1) and any foodstuff (9) with which it is reliably associated have been exposed to a pressure of about 20,000 psi or at least about 20,000 psi.

As to particular embodiments, the preselected pressure threshold can be about 30,000 psi or at least about 30,000 psi; correspondingly, the dye (3) and the developer (4) can interact to form the visibly colored dye-developer complex (7) and provide a visible color change (6) when exposed to a pressure of about 30,000 psi or at least about 30,000 psi, thereby indicating that the pressure sensor (1) and any foodstuff (9) with which it is reliably associated have been exposed to a pressure of about 30,000 psi or at least about 30,000 psi.

As to particular embodiments, the preselected pressure threshold can be about 40,000 psi or at least about 40,000 psi; correspondingly, the dye (3) and the developer (4) can interact to form the visibly colored dye-developer complex (7) and provide a visible color change (6) when exposed to a pressure of about 40,000 psi or at least about 40,000 psi, thereby indicating that the pressure sensor (1) and any foodstuff (9) with which it is reliably associated have been exposed to a pressure of about 40,000 psi or at least about 40,000 psi.

As to particular embodiments, the preselected pressure threshold can be about 50,000 psi or at least about 50,000 psi; correspondingly, the dye (3) and the developer (4) can interact to form the visibly colored dye-developer complex (7) and provide a visible color change (6) when exposed to a pressure of about 50,000 psi or at least about 50,000 psi, thereby indicating that the pressure sensor (1) and any foodstuff (9) with which it is reliably associated have been exposed to a pressure of about 50,000 psi or at least about 50,000 psi.

As to particular embodiments, the preselected pressure threshold can be about 60,000 psi or at least about 60,000 psi; correspondingly, the dye (3) and the developer (4) can interact to form the visibly colored dye-developer complex (7) and provide a visible color change (6) when exposed to a pressure of about 60,000 psi or at least about 60,000 psi, thereby indicating that the pressure sensor (1) and any foodstuff (9) with which it is reliably associated have been exposed to a pressure of about 60,000 psi or at least about 60,000 psi.

As to particular embodiments, the preselected pressure threshold can be about 70,000 psi or at least about 70,000 psi; correspondingly, the dye (3) and the developer (4) can interact to form the visibly colored dye-developer complex (7) and provide a visible color change (6) when exposed to a pressure of about 70,000 psi or at least about 70,000 psi, thereby indicating that the pressure sensor (1) and any foodstuff (9) with which it is reliably associated have been exposed to a pressure of about 70,000 psi or at least about 70,000 psi.

As to particular embodiments, the preselected pressure threshold can be about 80,000 psi or at least about 80,000 psi; correspondingly, the dye (3) and the developer (4) can interact to form the visibly colored dye-developer complex (7) and provide a visible color change (6) when exposed to a pressure of about 80,000 psi or at least about 80,000 psi, thereby indicating that the pressure sensor (1) and any foodstuff (9) with which it is reliably associated have been exposed to a pressure of about 80,000 psi or at least about 80,000 psi.

As to particular embodiments, the preselected pressure threshold can be about 90,000 psi or at least about 90,000 psi; correspondingly, the dye (3) and the developer (4) can interact to form the visibly colored dye-developer complex (7) and provide a visible color change (6) when exposed to a pressure of about 90,000 psi or at least about 90,000 psi, thereby indicating that the pressure sensor (1) and any foodstuff (9) with which it is reliably associated have been exposed to a pressure of about 90,000 psi or at least about 90,000 psi.

As to particular embodiments, the preselected pressure threshold can be about 100,000 psi or at least about 100,000 psi; correspondingly, the dye (3) and the developer (4) can interact to form the visibly colored dye-developer complex (7) and provide a visible color change (6) when exposed to a pressure of about 100,000 psi or at least about 100,000 psi, thereby indicating that the pressure sensor (1) and any foodstuff (9) with which it is reliably associated have been exposed to a pressure of about 100,000 psi or at least about 100,000 psi.

As but one non-limiting example, the preselected pressure threshold can be about 87,000 psi; correspondingly, the dye (3) and the developer (4) can interact to form the visibly colored dye-developer complex (7) and provide a visible color change (6) when exposed to a pressure of about 87,000 psi, thereby indicating that the pressure sensor (1) and any foodstuff (9) which it is reliably associated with have been exposed to a pressure of at least about 87,000 psi.

As to particular embodiments, the pressure sensor (1) can include a plurality of populations of encapsulated or microencapsulated color-changing systems (11), whereby each population has a characteristic preselected pressure threshold to which it reacts to provide a visible color change (6).

As but one illustrative example, a first population of encapsulated or microencapsulated color-changing systems (11) can provide a visible color change (6) at a relatively low preselected pressure threshold (e.g., 15,000 psi) and a second population of encapsulated or microencapsulated color-changing systems (11) can provide a visible color change (6) at a relatively high preselected pressure threshold (e.g., 87,000 psi), whereby the first and second populations can have the same or different dyes contained within them.

As but a second illustrative example, a plurality of populations of encapsulated or microencapsulated color-changing systems (11), each having a characteristic preselected pressure threshold to which it reacts to provide a visible color change (6), can be disposed in an arrangement that facilitates observation of their color development, such as by arranging the populations sequentially in order of increasing preselected pressure threshold and by including indicia on or within the pressure sensor (1) that correlates color development of the populations with their associated preselected pressure threshold.

Additional Indicators

As to particular embodiments, the instant pressure sensor (1) can include other indicators (e.g., a temperature indicator or a moisture sensor) associated with it, so that the pressure-sensing functionality of the pressure sensor (1) can be combined with (for example) temperature-sensing functionality or moisture-sensing functionality.

Use of the Pressure Sensor

The instant pressure sensor (1) can be used with a method for visually determining whether a preselected pressure threshold has been achieved, for example during HPP treatment of a foodstuff (9). Also, the instant pressure sensor (1) can be used with a method for indicating or confirming achievement of a preselected pressure threshold, for example during HPP treatment of a foodstuff (9).

Each method includes reliably associating the pressure sensor (1) with a foodstuff (9). Further, each method can, but need not necessarily, include subjecting the foodstuff (9) and reliably associated pressure sensor (1) to HPP treatment. Further, each method can, but need not necessarily, include detecting whether or not the visible color change (6) occurred. As to particular embodiments, detecting whether or not the visible color change (6) occurred can include visually observing the pressure sensor (1).

Following, detection of the visible color change (6), for example by visual observation, can indicate that the preselected pressure threshold was achieved during HPP treatment. In contrast, detection of the absence of the visible color change (6), for example by visual observation, can indicate that the preselected pressure threshold was not achieved during HPP treatment.

The pressure sensor (1) can be reliably associated with a single foodstuff (9), a single package, a plurality of foodstuffs (9), or a plurality of packages. The method by which the pressure sensor (1) and the foodstuff (9) are reliably associated is not critical and practically any method of association that will retain association of the pressure sensor (1) and foodstuff(s) (9) during HPP treatment can be used.

By way of non-limiting example, the pressure sensor (1) can simply be placed loose in the vessel (8) used for HPP treatment and left there with the foodstuff (9) until dissociation is desired. However, it is typically preferable that the pressure sensor (1) remain associated with the foodstuff (9) following HPP treatment. To achieve this end, the pressure sensor (1) and foodstuff (9) can be associated in any way and using any devices typically used in the food processing industry. By way of non-limiting examples, the pressure sensor (1) can be adhered to, glued, tied, or otherwise attached to the foodstuff (9), packaging material, or package or to a container or rack that contains the foodstuff (9), packaging material, or package.

The pressure sensor (1) can be co-packaged with the foodstuff (9) or used to seal a package or container containing the foodstuff (9), such that the foodstuff (9) cannot be removed from the package or container without removing or breaking the pressure sensor (1). Likewise, the pressure sensor (1) can be part of, or contained within, a package used for commercial shipment, display, or sale of the foodstuff (9). By way of non-limiting example, the pressure sensor (1) can be sandwiched between two layers of flexible plastic film that are used to seal a foodstuff (9) for retail sale. In such an arrangement, the pressure sensor (1) is preferably sealed in a compartment distinct from (not fluidly communicable with) the compartment in which the foodstuff (9) is sealed.

By reliably associating the pressure sensor (1) and the foodstuff (9), the information displayed by the pressure sensor (1) (i.e., whether or not the preselected pressure threshold was achieved during HPP treatment) can remain associated with the foodstuff (9) and inform downstream users of the foodstuff (9) (i.e., food processing plant workers, retailers, or customers) regarding the HPP treatment status of the foodstuff (9).

Example 1

The subject matter of this disclosure is now described with reference to the following example. Of note, this example is provided for the purpose of illustration only, and the subject matter is not limited to this example, but rather encompasses all variations which are evident as a result of the teaching provided herein.

In order to test whether a particular embodiment of the instant pressure sensor (1) described herein could be used for visually determining whether a preselected pressure threshold has been achieved during HPP treatment or for indicating achievement of a preselected pressure threshold during HPP treatment, a pressure sensor (1) was developed and tested in a model HPP system.

The pressure sensor (1) included a microencapsulated thermochromic color-changing system (11) having the color-memory property as described above, comprising about 5-10% w/w 7-[4-(diethylamino)-2-ethoxyphenyl]-7-(1-ethyl-2-methylindol-3-yl)furo[3,4-b]pyridin-5-one (CAS No.: 69898-40-4) as the dye, about 10-20% w/w 4-[2-(4-hydroxyphenyl)-4-methylpentan-2-yl]phenol (CAS No.: 6807-17-6) as the developer, and about 70-85% w/w dodecanophenone (CAS No.: 1674-38-0) as the solvent, whereby the microencapsulated thermochromic color-changing system (11) was prepared as taught in U.S. Pat. Nos. 8,883,049, 9,175,175, and 9,695,320, each of which is hereby incorporated by reference herein.

The microencapsulated thermochromic color-changing system (11) was incorporated into an ink including JONCRYL® 142 (available from BASF) and SURFYNOL® 104 (available from Air Products). Following, the formulation was printed onto a substrate (15) configured as polypropylene film to provide the pressure sensor (1) for testing.

Following, each of five distinct pressure sensors (1) was coupled to a container to provide a pressure sensor-container construct which was then disposed/placed in a vessel (8) and subjected to HPP treatment, whereby each of the five distinct pressure sensor-container constructs was subjected to a different preselected pressure threshold (as shown in Table 1). Of note, the vessel (8) within which each pressure sensor-container construct was disposed/placed had an initial temperature of about 15° Celsius when at atmospheric pressure. Subsequent to achievement of each preselected pressure threshold, the vessel (8) was depressurized and returned to atmospheric pressure, and the effect on each pressure sensor (1) was observed.

Figure 4:
FIG. 4 is a photograph of experimental results obtained after subjecting five instant pressure sensor samples to HPP treatments of varying preselected pressure thresholds.

The results of the testing are shown in Table 1, whereby no color change was observed at 15,000 psi but a visible color change (6) was observed upon achievement of 25,000 psi, 35,000 psi, 45,000 psi, and 85,000 psi. Additionally, FIG. 4 is a photograph showing (i) no color change of Sample 1 and (ii) the visible color change (6) from colorless or substantially colorless to blue of Samples 2 through 5 upon achievement of their respective preselected pressure thresholds.

TABLE 1

| Sample Number | Preselected Pressure Threshold (psi) | Observation of Visible Color Change |
|---|---|---|
| 1 | 15,000 | no |
| 2 | 25,000 | yes |
| 3 | 35,000 | yes |
| 4 | 45,000 | yes |
| 5 | 85,000 | yes |

From the observations described and shown in this example, it was concluded that the instant pressure sensor (1) is suitable (i) for visually determining whether a preselected pressure threshold has been achieved during HPP treatment, and (ii) for indicating achievement of a preselected pressure threshold during HPP treatment.

Temperature of HPP Treatment

During HPP treatment, variable conditions include pressure as well as temperature. It should be appreciated that noted herein, the preselected pressure threshold of the color-changing system (2), which is the pressure at which the dye (3) and the developer (4) interact to form the visibly colored dye-developer complex (7), can be adjusted by altering the temperature of the HPP treatment. For example, by increasing the temperature of the HPP treatment, the preselected pressure threshold to which the color-changing system (2) reacts can be correspondingly increased. Conversely, by decreasing the temperature of the HPP treatment, the preselected pressure threshold to which the color-changing system (2) reacts can be correspondingly decreased.

Moreover, during HPP treatment, in addition to an increase in pressure, an increase in temperature may also be observed, which is an adiabatic process. For example, it may be expected that during HPP, adiabatic compression of water increases the temperature of the system by about 3 Celsius degrees for every 14,500 psi increase in pressure.

Following, consideration should be paid to the maximum temperature reached within the vessel (8) during HPP treatment to ensure that the maximum pressure does not equal or exceed $T_2$, at which point a sufficient amount of energy is input into the system to destabilize the visibly colored dye-developer complex (7).

As can be easily understood from the foregoing, the basic concepts of the present invention may be embodied in a variety of ways. The invention involves numerous and varied embodiments of a pressure sensor and methods for making and using such a pressure sensor.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "combination" should be understood to encompass disclosure of the act of "sensing"—whether explicitly discussed or not—and, conversely, were there effectively disclosure of the act of "sensing", such a disclosure should be understood to encompass disclosure of a "sensor" and even a "means for sensing". Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the pressure sensors herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application, if any, provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A pressure sensor for visually determining whether a pressure threshold has been achieved, said pressure sensor comprising:
    a color-changing system comprising:
        a dye;
        a developer; and
        a solvent;
    wherein said color-changing system is contained such that said dye, said developer, and said solvent are encapsulated together;
    wherein said developer variably interacts with said dye according to the pressure of said color-changing system; and
    wherein upon achievement of said pressure threshold, said dye and said developer interact, resulting in a visible color change.

2. The pressure sensor of claim 1, wherein said dye comprises a leuco dye.

3. The pressure sensor of claim 2, wherein said leuco dye changes between a substantially colorless state and a visibly colored state.

4. The pressure sensor of claim 3, wherein upon achievement of said pressure threshold, said leuco dye changes from said substantially colorless state to said visibly colored state.

5. The pressure sensor of claim 4, wherein said visibly colored state is retained upon said decrease in pressure from said pressure threshold.

6. The pressure sensor of claim 1, wherein said color-changing system is encapsulated within a capsule to provide an encapsulated color-changing system.

7. The pressure sensor of claim 6, wherein said color-changing system is encapsulated within a microcapsule to provide a microencapsulated color-changing system.

8. The pressure sensor of claim 7, wherein upon achievement of said selected pressure threshold, said microcapsule need not rupture to produce said visible color change.

9. The pressure sensor of claim 7, wherein upon achievement of said selected pressure threshold, said visible color change occurs within said microcapsule.

10. The pressure sensor of claim 1, wherein said color-changing system is incorporated into a coating.

11. The pressure sensor of claim 1, wherein said color-changing system is incorporated into an ink.

12. The pressure sensor of claim 1, wherein said coloring-changing system comprises a reversible color-changing system.

13. The pressure sensor of claim 12, wherein said reversible color-changing system comprises a color-memory property which facilitates retention of said visible color change upon a decrease in pressure from said pressure threshold to record said achievement of said pressure threshold.

14. The pressure sensor of claim 1, wherein said color-changing system comprises a thermochromic color-changing system.

15. A method for visually determining whether a pressure threshold has been achieved during high pressure processing treatment of a foodstuff, comprising:
reliably associating a pressure sensor with said foodstuff, said pressure sensor comprising:
a color-changing system comprising:
a dye;
a developer; and
a solvent;
wherein said color-changing system is contained such that said dye, said developer, and said solvent are encapsulated together;
wherein said developer variably interacts with said dye according to the pressure of said color-changing system; and
wherein upon achievement of said pressure threshold, said dye and said developer interact, resulting in a visible color change.

16. The method of claim 15, wherein said coloring-changing system comprises a reversible color-changing system.

17. The method of claim 16, wherein said reversible color-changing system comprises a color-memory property which facilitates retention of said visible color change upon a decrease in pressure from said pressure threshold to record said achievement of said pressure threshold.

18. The method of claim 15, wherein said color-changing system comprises a thermochromic color-changing system.

19. A method for indicating achievement of a pressure threshold during high pressure processing treatment of a foodstuff, comprising:
reliably associating a pressure sensor with said foodstuff, said pressure sensor comprising:
a color-changing system comprising:
a dye;
a developer; and
a solvent;
wherein said color-changing system is contained such that said dye, said developer, and said solvent are encapsulated together;
wherein said developer variably interacts with said dye according to the pressure of said color-changing system; and
wherein upon achievement of said pressure threshold, said dye and said developer interact, resulting in a visible color change.

20. The method of claim 19, wherein said coloring-changing system comprises a reversible color-changing system.

21. The method of claim 20, wherein said reversible color-changing system comprises a color-memory property which facilitates retention of said visible color change upon a decrease in pressure from said pressure threshold to record said achievement of said pressure threshold.

22. The method of claim 19, wherein said color-changing system comprises a thermochromic color-changing system.

* * * * *